(12) United States Patent
Ely et al.

(10) Patent No.: US 8,105,322 B2
(45) Date of Patent: Jan. 31, 2012

(54) REPLACEMENT CARTRIDGES FOR LIGHT-BASED DERMATOLOGIC TREATMENT DEVICES

(75) Inventors: Doug Ely, North Andover, MA (US); Daniel L. Roth, Boston, MA (US); Elias Behrakis, Dracut, MA (US)

(73) Assignee: Shaser, Inc., Woburn, MA (US)

( * ) Notice: Subject to any disclaimer, the term of this patent is extended or adjusted under 35 U.S.C. 154(b) by 979 days.

(21) Appl. No.: 12/056,786

(22) Filed: Mar. 27, 2008

(65) Prior Publication Data
US 2009/0234342 A1 Sep. 17, 2009

Related U.S. Application Data

(60) Provisional application No. 61/035,508, filed on Mar. 11, 2008.

(51) Int. Cl.
*A61B 18/18* (2006.01)
(52) U.S. Cl. ............... 606/9; 607/88; 607/89
(58) Field of Classification Search ......... 606/9; 607/88
See application file for complete search history.

(56) References Cited

U.S. PATENT DOCUMENTS

| | | | |
|---|---|---|---|
| 4,388,924 A | 6/1983 | Weissman et al. ............ 606/9 |
| 4,471,226 A | 9/1984 | Wisnosky et al. ........ 250/504 H |
| 4,872,263 A | 10/1989 | Etheredge, III |
| 5,005,287 A | 4/1991 | Ritter |
| 5,968,033 A | 10/1999 | Fuller et al. |
| 6,168,590 B1 | 1/2001 | Neev |
| 6,273,884 B1 | 8/2001 | Altshuler et al. |
| 6,458,867 B1 | 10/2002 | Wang et al. |
| 6,508,813 B1 | 1/2003 | Altshuler |
| 6,514,243 B1 | 2/2003 | Eckhouse et al. |
| 6,759,235 B2 | 7/2004 | Empedocles et al. ...... 435/288.7 |
| 6,770,069 B1 | 8/2004 | Hobart et al. |
| 7,040,774 B2 | 5/2006 | Beeson et al. ............ 362/84 |
| 7,097,639 B1 | 8/2006 | Almeida |
| 7,135,033 B2 | 11/2006 | Altshuler et al. |
| 7,220,254 B2 | 5/2007 | Altshuler et al. |
| 2001/0029364 A1 | 10/2001 | Almeida ...................... 606/9 |
| 2002/0035360 A1 | 3/2002 | Conners et al. |
| 2003/0010987 A1 | 1/2003 | Banin et al. ................. 257/82 |
| 2003/0220632 A1 | 11/2003 | Strasser et al. |
| 2004/0006332 A1 * | 1/2004 | Black ........................ 606/9 |
| 2004/0093042 A1 | 5/2004 | Altshuler et al. ........... 607/88 |
| 2004/0230260 A1 * | 11/2004 | MacFarland et al. ...... 607/89 |
| 2005/0045189 A1 | 3/2005 | Jay |

(Continued)

FOREIGN PATENT DOCUMENTS

EP 0 913 127 9/2000

(Continued)

OTHER PUBLICATIONS

U.S. Appl. No. 141,370, filed Jan. 26, 2006, Dover et al.

(Continued)

*Primary Examiner* — Henry M Johnson, III
*Assistant Examiner* — Jeffrey Lipitz
(74) *Attorney, Agent, or Firm* — Guerin & Rodriguez, LLP

(57) ABSTRACT

A dermatologic treatment device having a light source emitting optical radiation beneficial to at least one dermatologic treatment, a brightness enhancer enhancing the brightness of at least some of the emitted optical radiation, and a replacement cartridge containing the light source and brightness enhancer. The cartridge facilitating replacement of the light source and brightness enhancer by a user of the device between dermatologic treatments.

5 Claims, 10 Drawing Sheets

U.S. PATENT DOCUMENTS

| | | | |
|---|---|---|---|
| 2005/0063199 A1 | 3/2005 | Levy et al. | |
| 2005/0065579 A1 | 3/2005 | Chen et al. | 607/88 |
| 2005/0133740 A1 | 6/2005 | Gardner | |
| 2005/0191252 A1 | 9/2005 | Mitsui | 424/62 |
| 2005/0273089 A1 | 12/2005 | Kreindel et al. | |
| 2006/0113895 A1 | 6/2006 | Baroky et al. | 313/501 |
| 2006/0173362 A1* | 8/2006 | Toms et al. | 600/478 |
| 2006/0206103 A1 | 9/2006 | Altshuler et al. | 606/9 |
| 2007/0010726 A1* | 1/2007 | Loeb et al. | 600/317 |
| 2007/0129711 A1 | 6/2007 | Altshuler et al. | |
| 2007/0198004 A1 | 8/2007 | Altshuler et al. | |
| 2007/0219600 A1 | 9/2007 | Gertner et al. | |
| 2007/0276359 A1 | 11/2007 | Segal | |
| 2008/0058783 A1* | 3/2008 | Altshuler et al. | 606/9 |
| 2008/0103714 A1* | 5/2008 | Aldrich et al. | 702/81 |

FOREIGN PATENT DOCUMENTS

| | | |
|---|---|---|
| EP | 1535582 A1 | 6/2005 |
| EP | 1728534 A2 | 5/2006 |
| EP | 0960601 A2 | 10/2006 |
| GB | 2443470 A | 5/2008 |
| JP | 2001078999 A2 | 3/2001 |
| JP | 2008029811 A | 2/2008 |
| WO | WO9503089 | 2/1995 |
| WO | WO9851235 | 5/1998 |
| WO | WO02089688 | 11/2002 |
| WO | WO02094116 | 11/2002 |
| WO | WO 03/023472 A1 | 3/2003 |
| WO | WO 03/043514 A2 | 5/2003 |
| WO | WO 2004/067082 A2 | 8/2004 |
| WO | WO2004073537 | 9/2004 |
| WO | WO2006012605 | 2/2006 |
| WO | WO 2006/078613 A2 | 7/2006 |
| WO | WO 2007/007167 A1 | 1/2007 |
| WO | PCT/US07/19332 | 9/2007 |
| WO | WO 2007/099546 A2 | 9/2007 |
| WO | WO 2007/120229 A2 | 10/2007 |
| WO | WO 2008/002625 A2 | 1/2008 |
| WO | WO 2008/008971 A1 | 1/2008 |
| WO | WO 2008/020427 A2 | 2/2008 |
| WO | WO 2008/070747 A2 | 6/2008 |

OTHER PUBLICATIONS

PCT International Search Report based on PCT/US2005/026282 dated Feb. 9, 2006.

PCT International Search Report based on PCT/US08/04008 dated Jul. 30, 2008.

Office Action cited in U.S. Appl. No. 11/141,370 mailed May 18, 2010.

Office Action cited in U.S. Appl. No. 12/056,697 mailed Dec. 31, 2009.

Office Action cited in U.S. Appl. No. 12/056,697 mailed May 25, 2010.

Examination Report in foreign counterpart application No. GB0808101.0 dated Apr. 8, 2009 (2 pages).

Combined Search and Examination Report in foreign counterpart application No. GB0808101.0 dated Jul. 31, 2008 (5 pages).

UK Patent Office Search and Examination Report based on GB Patent Application No. GB 0808097.0 dated Jul. 30, 2008 (2 pages).

Office Action issued in U.S. Appl. No. 12/056,697, dated Nov. 16, 2010 (9 pages).

European Patent Office Supplementary Search Report based on EP Patent Application No. EP 08 74 2313 dated Jun. 11, 2011 (9 pages).

Office Action issued in U.S. Appl. No. 12/056,747, dated May 24, 2011 (11 pages).

Office Action issued in U.S. Appl. No. 12/056,649, dated Aug. 8, 2011 (9 pages).

* cited by examiner

REPLACEMENT CARTRIDGES FOR LIGHT-BASED DERMATOLOGIC TREATMENT DEVICES

RELATED APPLICATIONS

This claims priority to and the benefit of U.S. Provisional Patent Application No. 61/035,508 filed on Mar. 11, 2008, the entirety of which is incorporated herein by reference. This is also related to U.S. Patent application Ser. Nos. 12/056,612, 12/056,649, 12/056,697, 12/056,716, 12/056,747, and 12/056,816 all of which were filed on Mar. 27, 2008.

TECHNICAL FIELD

The disclosed technology relates generally to dermatologic treatments and more specifically to techniques for enhancing the performance of optical radiation systems used in such dermatologic treatments.

BACKGROUND

Electromagnetic energy has been used in a wide range of medical applications for many years. In the field of dermatology, lasers, flashlamps/intense pulsed light systems (IPL), and other sources of electromagnetic radiation, particularly in the optical radiation wavebands, have been used for permanently and temporarily removing hair, promoting hair regrowth, coagulating blood vessels visible through a patient's skin, treating lesions, removing port-wine stains, removing tattoos, rejuvenating skin, and the like. Optical radiation systems applied to such dermatologic treatments are normally operated by trained professionals who select the preferred energy level, wavelength(s), and other optical radiation parameters that are optimal for a particular treatment, given a patient's skin type and other factors, so as to effectuate the desired treatment while mitigating damage to nontarget tissue.

The ability to safely and efficiently service multiple patients of varying skin types and/or perform multiple types of dermatologic treatments comes at a significant cost, with many clinical systems in existence today exhibiting a price exceeding $50,000. Industry participants in this highly competitive market are constantly trying to balance the flexibility, efficacy, and safety of such systems with cost-reduction goals. Recent attempts to commercialize single-purpose dermatologic systems (e.g., for hair growth management and removal, hair regrowth, or skin rejuvenation) for the home-use, mass market have experienced limited success, with such relatively low-cost systems either still being too expensive for many consumers or exhibiting poor efficacy. Accordingly, continuing research and development is necessary to develop cost-effective, safe, and effective dermatologic treatment systems regardless of market segment.

SUMMARY

In one aspect, the disclosed technology can be used to enhance the brightness of a multi-wavelength light source incorporated within a dermatologic system to thereby increase its efficiency and reduce the power and filtering requirements of the system resulting in an overall reduction in the size and cost of the system. Other aspects of the disclosed technology can enhance a user's experience with the dermatologic system by reducing the user's pain sensation when using the system during a dermatologic treatment and/or facilitating the movement of the system across a skin surface under treatment.

In one illustrative embodiment, the disclosed technology can be used to enhance the optical radiation applied to a skin surface to facilitate a dermatologic treatment. In such an embodiment, a light source is provided which emits optical radiation having multiple wavelengths, where such emitted light has a first set of wavelengths that is preferred for a particular dermatologic treatment as well as other sets of wavelengths that are less desirable/undesirable for the treatment. At least some of the optical radiation exhibiting such undesirable wavelengths is reflected back to the light source to enhance the overall brightness of the emitted optical radiation. The enhanced optical radiation can be filtered to substantially remove any light exhibiting the undesirable wavelengths from the enhanced optical radiation applied to the skin surface during the dermatologic treatment. Alternatively, at least some of the light exhibiting the undesirable wavelengths can be converted into light exhibiting the preferred first set of wavelengths prior to application of the enhanced optical radiation to the skin surface. The optical radiation applied to the skin surface can further be diffused. The light source itself can be automatically energized at predetermined intervals during the dermatologic treatment to, for example, produce a strobe effect. Emission of optical radiation may also be enabled in response to detecting a contact with the skin surface. Further, a vibration can be applied to the skin surface to reduce the pain sensation experienced by a user/patient during the dermatologic treatment.

In another illustrative embodiment, the disclosed technology is embodied within a system adapted to enhance the brightness of optical radiation applied to a skin surface to facilitate a dermatologic treatment. The disclosed system includes a first reflector that reflects at least some optical radiation (preferably exhibiting multiple wavelengths) emitted by a light source (e.g., one or more flashlamps, one or more light-emitting diodes, etc.) back to the light source so as to enhance the brightness of the emitted optical radiation. At least some of the enhanced optical radiation is conveyed through a contact element in contact with a skin surface to facilitate a desired dermatologic treatment.

In some dermatologic treatments (e.g., permanent/temporary hair removal), the enhanced optical radiation includes at least some wavelengths in the near infrared portion of the electromagnetic spectrum. The optical radiation may exhibit sets of wavelengths that are preferable for different dermatologic treatments. For example, a first set of wavelengths may be preferred for a particular dermatologic treatment, such as hair removal, while a second set of wavelengths may be preferred for a different dermatologic treatment, such as treatment of psoriasis. The optical radiation reflected by the reflector back to the light source may include all wavelengths, primarily the set of wavelengths that are not desired for a particular dermatologic treatment, or any other combination of wavelengths.

A particularly advantageous arrangement for this illustrative embodiment would have the first reflector reflect primarily undesirable wavelength sets back to the light source and allow optical radiation exhibiting a first set of preferred wavelengths to pass the reflector without any substantially material affect. In this embodiment, a second reflector can be positioned to reflect at least some of the optical radiation exhibiting the first set of preferred wavelengths towards the skin surface. The first reflector may be further arranged in a tubular shape that substantially surrounds the light source and the second reflector may be preferably arranged in an ellipsoid shape. Alternatively, the first reflector may be arranged in a planar shape and the second reflector may be arranged in a paraboloid shape.

The contact element that is in contact with the skin surface during the dermatologic treatment is configured to be optically transparent to the optical radiation exhibiting the first set of preferred wavelengths. The contact element may include a hydrophilic portion that facilitates the dermatologic treatment (e.g., facilitates gliding of the dermatologic system over the skin surface being treated) and may further diffuse the optical radiation conveyed by the contact element when the hydrophilic portion is exposed to water. The disclosed system may further include a timing circuit to energize the light source at predetermined intervals during the dermatologic treatment, a contact sensor detecting a contact between the contact element and the skin surface and adapted to transmit a control signal in response to such contact to enable the light source to be energized, and/or a vibrating element adapted to apply a vibration to the skin surface to reduce pain sensation experienced by a user/patient during the dermatologic treatment. In a particularly advantageous arrangement, the contact element both conveys optical radiation having a preferred set of wavelengths to which it is optically transparent and applies the vibration to the skin surface being treated to reduce the pain sensation experienced by the user/patient during the dermatologic treatment.

In yet another illustrative embodiment, the disclosed technology is embodied within a system that includes a light source, a brightness-enhancing element in optical communication with the light source, and a contact element adapted to be in contact with the skin surface being treated by the dermatologic treatment system. The light source emits optical radiation (e.g., with at least one wavelength in the near infrared portion of the electromagnetic spectrum) that is beneficial to the dermatologic treatment and the brightness-enhancing element is adapted to increase the brightness of this emitted optical radiation during the treatment. The contact element is adapted to provide a vibration to the skin surface to reduce a pain sensation resulting from application of the brightness-enhanced optical radiation to the skin surface. The disclosed system further includes a handheld housing that contains the light source and brightness-enhancing element and is configured to maintain a relative orientation between the light source, brightness-enhancing element, and contact element during the dermatologic treatment.

In yet another illustrative embodiment, the disclosed technology can be embodied within a system that includes an electromagnetic source emitting electromagnetic radiation (e.g., optical radiation) that is beneficial to a dermatologic treatment, a vibration element that provides a vibration to a skin surface to reduce a sensation resulting from application of the electromagnetic radiation to the skin surface during the dermatologic treatment, and a handheld housing that contains the electromagnetic source and maintains a relative orientation between such source and the vibration element during the dermatologic treatment. The vibration element may also be contained within the handheld housing and/or may further provide a haptic feedback to the user of the system. The haptic feedback substantially coincides with the application of the emitted optical radiation to the skin surface during the dermatologic treatment.

In yet another illustrative embodiment, the disclosed technology can be embodied within a system that includes a source of electromagnetic radiation that is beneficial to a dermatologic treatment. This system further includes a contact element that facilitates conveyance of at least some of the electromagnetic radiation emitted by the source to a skin surface and where the contact element preferably includes a hydrophilic portion that facilitates its movement to/onto the skin surface. The hydrophilic portion of the contact element can also be formulated to filter at least some of the electromagnetic radiation to substantially inhibit conveyance of at least some undesirable wavelengths to the skin surface. The hydrophilic portion can also diffuse the electromagnetic energy prior to its conveyance to the skin surface.

In yet another illustrative embodiment, the disclosed technology can be embodied within a dermatologic treatment device that includes at least a light source (e.g., one or more flashlamps and/or light emitting diodes), a wavelength converter, and a contact element. The light source emits optical radiation exhibiting a first set of wavelengths (e.g., at least some of such wavelengths can be in the near infrared portion of the electromagnetic spectrum) that are preferred for a dermatologic treatment and other sets of wavelengths that are less desirable or undesirable. The wavelength converter converts at least some of these other, less desirable/undesirable wavelengths (which may exhibit shorter wavelengths than those in the first set) into the preferred wavelengths of the first set. The wavelength converter preferably includes a composition of quantum dots having a core comprised of, for example, CdTe, InAs, InP, InSb, PbS, PbSe, or the like. The core of such quantum dots can be further encapsulated in one or more overcoating layers comprised of, for example, ZnS, ZnSe, GaN, MgS, MgSe, MgTe, CdS, CdSe, or the like. Such overcoating layers are preferably selected so as not to substantially modify the wavelength emissions of the core. The composition of quantum dots in the wavelength converter can be arranged so at least some of the optical radiation with undesirable/less desirable wavelengths exhibiting relatively longer wavelengths are converted into the first set of preferred wavelengths prior to conversion of that portion of the undesirable/less desirable wavelengths exhibiting relatively shorter wavelengths. The wavelength converter may be further adapted to conduct heat away from the light source. The contact element conveys at least some of the converted optical radiation to a one or more skin surfaces to facilitate the dermatologic treatment.

In yet another illustrative embodiment, the disclosed technology can be embodied within dermatologic treatment devices that facilitate one or more dermatologic treatments of interest. The device includes a handheld housing that contains a light source which emits optical radiation beneficial to the dermatologic treatment(s). The housing also preferably adapted to provide a haptic feedback to a user of the device that substantially coincides with an application of the emitted optical radiation to a skin surface during the dermatologic treatment.

In yet another illustrative embodiment, the disclosed technology can be embodied within a dermatologic treatment device that includes a light source (e.g., laser, light emitting diode, flashlamp, etc.) emitting optical radiation beneficial to a dermatologic treatment and a user interface that selectively operates the device in pulse mode or strobe mode. In pulse mode, the light source emits a single optical radiation pulse to facilitate a spot treatment on a portion (e.g., 2 square centimeters) of a skin surface during the dermatologic treatment. In strobe mode, the light source emits a continuous sequence of optical radiation pulses to facilitate treatment of multiple locations on the skin surface during the dermatologic treatment. In one exemplary implementation, the duration of each pulse in the sequence can be 50 ms and the interpulse delay can be one second.

In yet another illustrative embodiment, the disclosed technology can be embodied within a dermatologic treatment device that includes a light source, brightness enhancer, and replacement cartridge. The light source (e.g., laser, light emitting diode, flashlamp, etc.) emits optical radiation that is beneficial to one or more dermatologic treatments and the brightness enhancer enhances the brightness of at least some of this emitted optical radiation. The replacement cartridge contains the light source and the brightness enhancer to facilitate their replacement by a user of the device between dermatologic treatments. The replacement cartridge is designed to be insertable into or removed from a handheld housing of the device. The replacement cartridge can also be designed for a particular skin type, which can be replaced prior to treating a different skin type and/or prior to treating different skin surfaces of the user during the same dermatologic treatment session.

In yet another illustrative embodiment, the disclosed technology can be embodied within a dermatologic treatment device that includes a light source, a reflector, a thermally conductive material, and a replacement cartridge. The light source emits at least some radiation which is beneficial to one or more dermatologic treatments, including optical radiation that exhibits a first set of wavelengths that are preferred for the dermatologic treatment(s) and a second set of wavelengths that are undesirable/less desirable for the treatment(s). The reflector is optically coupled to the light source and reflects the emitted optical radiation in a predetermined manner. The thermally conductive material is in thermal communication with the light source and reflector and facilitates a transfer of heat from the light source to the reflector. The thermally conductive material can include a composition of quantum dots adapted to convert at least some of the undesirable/less desirable second set of wavelengths into preferred first set of wavelengths. The replacement cartridge contains the light source, reflector, and thermally conductive material thereby facilitating the replacement of these components by a user of the device between dermatologic treatments. The replacement cartridge is insertable into/removable from a handheld housing of the device. The replacement cartridge can be designed for a particular skin type and may be further replaced prior to treating a different skin type and/or prior to treating different skin surfaces of the user during the same dermatologic treatment session.

In yet another illustrative embodiment, the disclosed technology can be embodied within a dermatologic treatment device that includes a first light source, a second light source, and a timing circuit. The first light source emits a first pulse of optical radiation beneficial to a dermatologic treatment. The second light source is optically coupled to the first light source and emits a second pulse that enhances the brightness of at least part of the optical radiation in the first pulse upon impinging on the first light source. The first pulse can further enhance the brightness of at least part of the optical radiation in the second pulse upon impinging on the second light source. The timing circuit is adapted to energize the first and second light sources to at least partially overlap emissions of the first and second pulses (resulting in, for example, a combined duration in the aggregate light pulse actually conveyed to a skin surface of about 50 ms). The first and second light sources can be of the same or different type. The first and second pulses may also have one or more wavelengths in common or may not exhibit any common wavelengths. The device may further include a contact element that is optically coupled to the first and second light sources and directs the at least partially overlapping emissions of the first and second pulses to a skin surface during the dermatologic treatment.

BRIEF DESCRIPTION OF THE DRAWINGS

The foregoing discussion will be understood more readily from the following detailed description of the disclosed technology, when taken in conjunction with the accompanying drawings in which.

DETAILED DESCRIPTION

Figure 1:
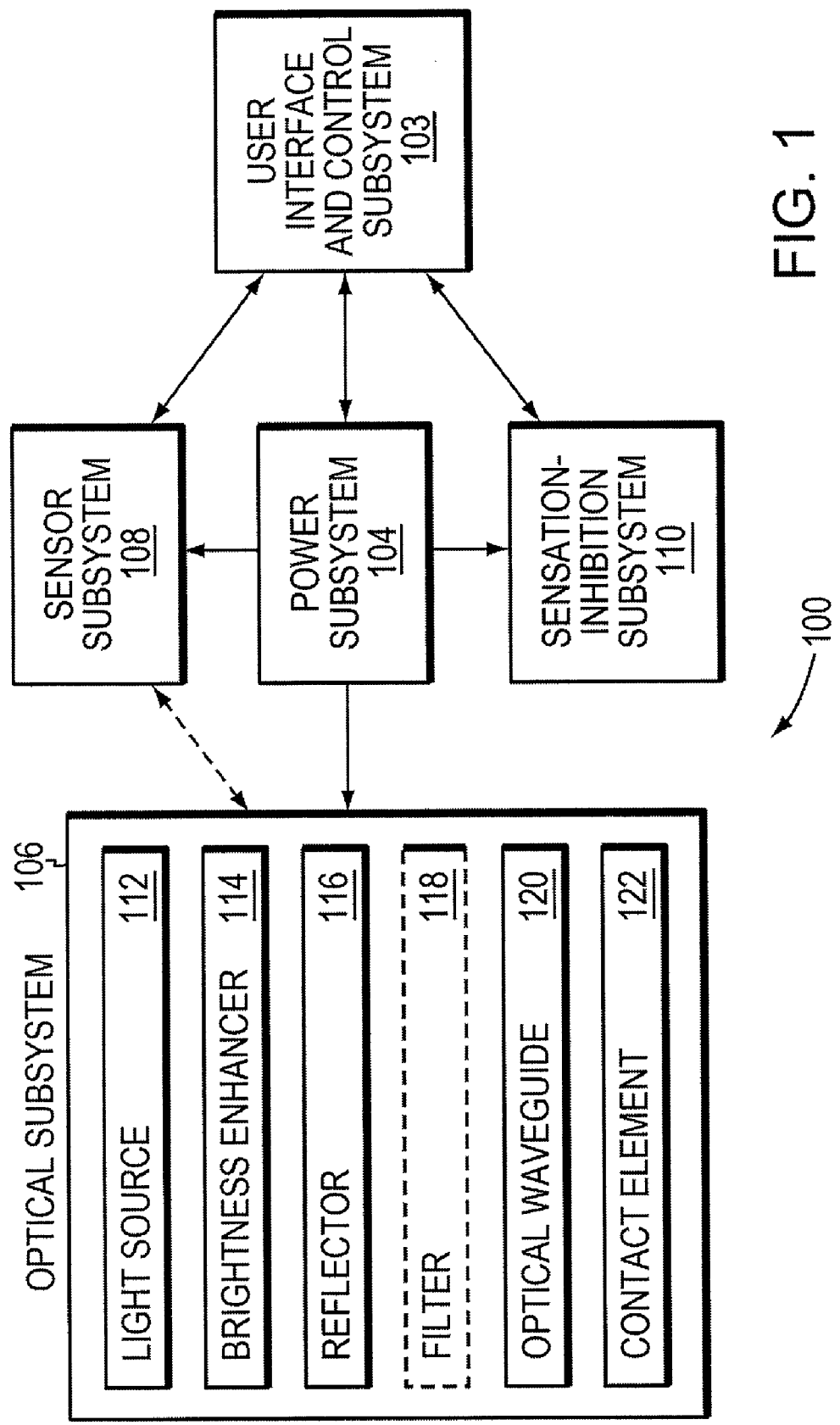
FIG. 1 provides a high-level block diagram of an illustrative dermatologic treatment device operated in accordance with the disclosed technology.

Unless otherwise specified, the illustrated embodiments can be understood as providing exemplary features of varying detail of certain embodiments, and therefore, unless otherwise specified, features, components, modules, elements, and/or aspects of the illustrations can be otherwise combined, interconnected, sequenced, separated, interchanged, positioned, and/or rearranged without materially departing from the disclosed systems or methods. Additionally, the shapes and sizes of components are also exemplary and unless otherwise specified, can be altered without materially affecting or limiting the disclosed technology.

For the purposes of this disclosure, the term "subsystem" refers to a set of hardware and/or software elements that perform a desired functionality. Those skilled in the art will recognize that the functionality described for a particular subsystem can be incorporated into one or more other subsystems and that the subsystems themselves can be otherwise combined, separated, and/or organized without adversely affecting the operation of the disclosed technology and thus are intended merely for illustrative purposes. The term, "substantially" can be broadly construed to indicate a precise relationship, condition, arrangement, orientation, and/or other characteristic, as well as, deviations thereof as understood by one of ordinary skill in the art, to the extent that such deviations do not materially affect the disclosed methods and systems. Further, the terms "light" and "optical radiation" are used interchangeably and references to "wavelengths" pertain to optical radiation exhibiting wavelengths of the type described in that context. The terms "device" and "system" are also used interchangeably.

The suitability of treating medical/aesthetic problems with optical radiation has been investigated for several decades and spans a broad range of treatment scenarios. Indeed many laser and flashlamp-based systems have been commercialized and designed for operation by experienced health care professionals in the performance of both medical procedures (e.g., laser surgery, diagnosis and treatment of cancers, etc.) and cosmetic dermatologic treatment procedures (e.g., hair removal, hair regrowth, skin rejuvenation, tattoo removal, treatment of port-wine stains, etc.). The plethora of special and general-purpose devices that have been developed and commercialized by several industry participants coupled with stagnant market growth provide strong indicia that the clinical light-treatment market is substantially saturated and has matured.

In an effort to penetrate new market segments, some industry participants have recently focused their development efforts on producing light-based, home-use products designed for treatment of cosmetic dermatologic problems (e.g., removal of excess hair) by consumers without requiring specialized health care training. Such home-use products are preferably designed to perform a single cosmetic dermatologic procedure at a relatively low cost and incorporate safety and other design features to mitigate the risk of adverse affects to substantially untrained users. For example, a home-use, light-based device for temporarily removing hair should be designed to provide sufficient optical radiation to effect a desired change in the hair growth cycle without substantially damaging non-target tissue and while concurrently incorporating contact sensors, diffusing mechanisms, and/or other safety mechanisms to mitigate the risk of eye damage. In developing commercially viable hair removal devices for the home-use market, it is also important to incorporate features into such devices to enhance a user's experience when operating the device, such as employing a sufficiently large treatment coverage area and a reasonably quick treatment rate so that a user can treat large areas of skin in a short period of time, along with sensation inhibition technology to reduce the amount of pain experienced by the user during treatment, mobility technology to enhance a user's ability to move and manipulate the device while treating different skin surfaces, etc. The commercial success of such home-uses devices is largely dependent on providing the above features in a relatively small and inexpensive package.

As will be appreciated by those skilled in the art, providing an effective, safe, and feature-rich, home-use device in a small and relatively inexpensive package presents significant challenges and requires careful balancing of design choices. For example, design tradeoffs for a light-based temporary hair removal device for home-use may involve balancing the efficiency of the optical subsystem and ability to generate optical radiation of sufficient characteristics to treat various skin types versus cost of optical components and associated power, cooling, filtering, weight, and size requirements. Device costs generally increase with optical components exhibiting relatively high efficiencies, light sources providing optical radiation at preferred wavelengths with reduced filtering requirements, power components requiring greater output power and stringent pulse forming capabilities, effective techniques for high temperature cooling applications (liquid cooling being more complex and expensive than air cooling), etc.

In brief overview, an exemplary implementation of the disclosed technology can be used to develop such safe, effective, comfortable, and low cost hair growth management/removal devices by a) employing a relatively low-efficiency, low cost, multi-wavelength light source suitable for treating multiple skin and hair types, b) increasing the efficiency of the light source using light recycling techniques to enhance its brightness (i.e., spectral radiance) and thereby reduce power and filter requirements, c) optionally converting optical radiation exhibiting undesired wavelengths into preferred wavelengths (while, preferably, integrating the optical radiation such that it exhibits a substantially uniform light distribution at substantially the same time as the wavelength conversion), d) using a skin contact component of the device for dual purposes—facilitating the conveyance of optical radiation and concurrently inhibiting a user's pain sensation during the dermatologic treatment, e) providing multiple operating modes to cover spot treatments or large area treatments, and/or f) providing a mechanism that both facilitates movement of the device over a skin treatment surface by reducing the coefficient of friction at the skin-device interface without use of messy gels/lotions and concurrently diffuses the optical radiation to mitigate the risk of potential eye damage.

More particularly, the light source used in this illustrative embodiment is a flashlamp (e.g., xenon, krypton or the like) exhibiting an efficiency in wavelengths of interest of, for example, between about 10-20% and emitting optical radiation having wavelengths at least in the near infrared portion of the electromagnetic spectrum suitable for hair growth management/removal dermatologic treatments. The flashlamp is at least partially surrounded by multiple reflective coatings that are designed to reflect optical radiation exhibiting wavelengths that are not desired (e.g., ultraviolet) for the dermatologic treatment back to the plasma of the flashlamp while allowing preferred wavelengths (e.g., near infrared) to pass substantially unimpeded. In this manner, the reflective coatings provide a mechanism that both reflectively filters out a substantial amount of unwanted wavelengths and recycles these unwanted wavelengths so that they are superposed on the directly-emitted optical radiation to increase the brightness (spectral radiance) of the optical radiation, thereby resulting in an improved efficiency in the flashlamp without providing additional electrical current to the flashlamp. This technique of superposing unwanted radiation back onto the directly-emitted optical radiation emitted by the light source preferably results in a flashlamp efficiency in the wavelengths of interest that significantly exceeds 20%. The improved efficiency of the light source in the wavelengths of interest improves the efficacy of the device in performing the dermatologic treatment and reduces the size and capacity requirements of the power supply that is used to energize the flashlamp—resulting in reduced cost and size in the overall dermatologic treatment device.

The reflective coatings can be positioned on the inside or outside surface of the flashlamp itself, on the inside or outside surfaces of a tube surrounding the flashlamp, on a planar surface of an optical waveguide (e.g., a light pipe with a quadrilateral cross-section) receiving the emitted optical radiation, or in any other manner in which at least some optical radiation can be reflected back to the light source. In some embodiments, the reflection of optical radiation back to the light source may involve a single coating that reflects only a small portion of the unwanted radiation back to the source. In other embodiments, a reflector that partially surrounds the flashlamp can be polished aluminum, silver, gold or other type of reflector that reflects back substantially all of the wavelengths impinging on its reflective surface. Regardless of implementation details, the above light recycling technique increases the efficiency of a relatively low-cost and otherwise inefficient (in the wavelength band of interest) optical radiation source beyond its capabilities in normal operation and thereby improves performance of the optical subsystem while simultaneously reducing power, filtration, and other costs of the overall dermatologic treatment device. Any undesirable wavelengths that unwittingly pass by the reflective coatings can be, optionally, converted to desired wavelengths by subjecting these undesirable wavelengths to suitable phosphors, quantum dot materials or conveying such radiation through an optical waveguide doped with such quantum dots or other luminescent dopant materials designed to convert such undesired wavelengths to preferred wavelengths. Alternatively, the undesired wavelengths may be filtered out using one or more absorptive or reflective filters.

The illustrative embodiment described above can further include an optically-transparent, skin contact element that is placed substantially in physical contact with a skin surface during the dermatologic treatment. The contact element (e.g., a glass or plastic window supported within a handheld housing) facilitates conveyance of the optical radiation to the skin surface, while concurrently providing a vibration to the skin surface and/or surrounding skin surfaces so as to reduce the user's sensation of pain during the dermatologic treatment pursuant to the Gate Theory of Afferent Inhibition. This contact element may further include a hydrophilic substrate coating on the skin contacting surface that substantially reduces the coefficient of friction at the skin-device interface when exposed to water, thereby facilitating movement of the device between skin treatment regions. Upon exposure to water, this normally clear hydrophilic coating can appear cloudy and will thus further diffuse the optical radiation prior to its application to the skin surface resulting in greater safety from potential eye damage. The hydrophilic coating can also be formulated to filter out ultraviolet and other unwanted wavelengths. The contact element is also preferably adapted to be user-replaceable such that it can be periodically replaced when, for example, the optical properties of the element degrade, the element exhibits physical wear, a user completes a dermatologic treatment session (replacement reduces cleanup effort following the treatment and is more sanitary), the dermatologic treatment device is applied to the skin surface of a different user (again, replacement in such situations is more sanitary).

With reference now to FIG. 1, at least some aspects of the disclosed technology can be embodied within an illustrative hair growth management/removal device 100. The device 100 preferably includes a User Interface and Control Subsystem 102 that detects a user's intention to operate the device 100 and, in response, enables a Power Subsystem 104 to energize an Optical Subsystem 106 that generates and applies the desired optical radiation to the skin surface targeted for hair growth management, along with energizing a Sensor Subsystem 108 that ensures the safe operation of the device 100 and a Sensation-Inhibition Subsystem 110 that is adapted to inhibit the pain or other sensation experienced by the user of the device 100 during the dermatologic treatment.

The User Interface and Control Subsystem 102 preferably includes a mode selection capability such that the device 100 selectively operates in either pulse mode or strobe mode. In pulse mode, the User Interface and Control Subsystem 102 enables the Power Subsystem 104 to discharge sufficient electrical energy to the Optical Subsystem 106 such that a single pulse of optical radiation is generated and applied to a target skin surface. Conversely, in strobe mode, the User Interface and Control Subsystem 102 enables the Power Subsystem 104 to discharge electrical energy to the Optical Subsystem 106 at a preferably predetermined rate (e.g., one second inter-pulse intervals at a duration of between about 10-50 milliseconds per pulse) such that optical radiation is generated in a continuous sequence of corresponding light pulses. The interval between such light pulses is preferably sufficient to enable the user of the device 100 to apply each subsequent pulse to substantially adjacent skin surfaces so that a relatively large region of skin can be quickly subjected to the desired dermatologic treatment in a substantially gliding motion. A one second inter-pulse interval is preferred in both achieving this gliding motion and in providing a sufficient thermal relaxation time to prevent undesired tissue damage to treated skin surfaces in the event the user mistakenly applies multiple pulses to the same skin surface without providing sufficient time for the treated skin to dissipate its excess heat. In other illustrative embodiments, the User Interface and Control Subsystem 102 can enable the Power Subsystem 104 to discharge electrical pulses to the Optical Subsystem at a rate dependent on a user's movement of at least part of the device 100.

The illustrative User Interface and Control Subsystem 102 described above also enables the Power Subsystem 104 to energize the Sensor Subsystem 108, which, for example, detects whether the various components of the device 100 are operating within specified parameters (e.g., sense and evaluate the characteristics of emitted optical radiation and/or characteristics of optical radiation reflected back from the skin surface under treatment, etc.) and/or whether the device 100 is being properly operated by the user during the dermatologic treatment (e.g., sense whether at least part of the device 100 is in physical contact with the skin surface during treatment, etc.). Exemplary elements of the Sensor Subsystem 108 capable of confirming such physical contact may include one or more contact switches, capacitive sensors, resistive sensors, etc.

Similarly, the User Interface and Control Subsystem 102 enables the Power Subsystem 104 to energize the Sensation-Inhibition Subsystem 110, which preferably includes vibrating elements in physical contact with skin contact surfaces of the device 100 (e.g., one or more elements of the Optical Subsystem 106 and/or with a housing enclosing at least part of the device 100, etc.), such that vibrations of a sufficient magnitude and at a sufficient frequency (e.g., 5700 vibrations per minute) are applied to the skin surface under treatment and/or to substantially adjacent skin surfaces so as to reduce the user's overall sensation (e.g., sensations of pain, tingling, heat, etc.) during the dermatologic treatment. The vibrations applied to the skin surface by the device 100 can be continuous during the operation of the device 100 (including, for example, during a user's movement of parts of the device over the skin surface), can be restricted to a time interval that corresponds substantially to the same time interval and duration of the light pulse when applied to the skin surface, or can be applied during a time interval that begins shortly before the beginning of the light pulse and end shortly after the end of the light pulse (e.g., duration of light pulse+10 ms on each side thereof). The vibrations can further provide haptic feedback to the user of the device 100 so that the user can readily discern that a particular skin surface has been treated and that at least part of the device should therefore be moved to another skin surface. This haptic feedback is of particular relevance in situations where the vibrations dull the user's sensations in a particular skin surface/region to a degree that the user feels little or substantially no sensation from application of the light pulse to that skin surface/region and/or in situations where the light pulse applied to the skin surface/ region contains one or more wavelengths that may not be detectable by the human eye. Illustrative embodiments of the Sensor Subsystem 108 and Sensation-Inhibition Subsystem 110 are further described below in connection with FIG. 4.

The User Interface and Control Subsystem 102 is further adapted to receive feedback from the Power Subsystem 104, Sensor Subsystem 108, and/or Sensation-Inhibition Subsystem 110 and provide discernible indicia of at least some of the operating parameters of one or more of these subsystems to the user of the device 100. For example, mode (e.g., pulse mode, strobe mode, etc.), status (e.g., device operational, sufficient contact at skin-device interface, etc.), and/or error/fault information (e.g., component of one or more subsystems requires replacement, etc.) can be conveyed to the user via visible (e.g., LCD or other display types, illumination of one or more LEDs, etc.), audible (e.g., beeps, synthesized speech, recorded speech, etc.), haptic (e.g., vibration or other type of tactile stimulus), and/or any other type of user-discernible indicia.

The Power Subsystem 104 can be a line-powered supply which converts alternating current to one or more direct currents suitable for operating the various subsystems 102-110 of the device 100 or it can be a battery-powered supply with/without a line-power recharge capability that is adapted to convert direct current exhibiting a first amplitude to one or more other amplitudes as required by the various subsystems 102-110. Regardless of the source of electrical energy, the Power Subsystem 104 is preferably adapted to accommodate both the relatively low power requirements of the User Interface and Control Subsystem 102, Sensor Subsystem 108, and Sensation-Inhibition Subsystem 110 and the much greater power requirements of the Optical Subsystem 106. For example, the Power Subsystem 104 may include one or more power supplies with power transformation, rectification, regulation, and/or conditioning circuits, along with high voltage capacitors (in the case of flashlamp embodiments) and/or pulse forming circuitry to drive elements of the Optical Subsystem 106. The design of a suitable Power Subsystem 104 is well within the understanding of those skilled in the art and, therefore, is not given any further treatment in this disclosure.

An illustrative Optical Subsystem 106 includes a) one or more light sources 112 capable of generating optical radiation suitable for hair growth management/removal or other dermatologic treatment, b) one or more brightness-enhancers 114 that enhance the brightness of the optical radiation emitted by the light sources 112 and therefore increase its overall efficiency, c) one or more reflectors 116 (made of, for example, polished aluminum, gold, silver or other type of metallic or nonmetallic reflecting element, and shaped as a parabaloid, ellipsoid, or other suitable shape) adapted to reflect the normal and enhanced optical emissions of the light sources 112, d) one or more optical waveguides 120 (e.g., glass or plastic light pipes exhibiting a quadrilateral cross section, hollow optical waveguides with reflective internal surfaces, or any other type of elements that can efficiently convey optical radiation) preferably adapted to exhibit a relatively high total internal reflectance and which efficiently receive and convey optical radiation from the reflectors 116, and/or e) one or more contact elements 122 (made of glass, sapphire, plastic, or other materials that are optically transparent to wavelengths of interest and which may be formed in a variety of shapes and surfaces, e.g., flat, convex, concave, etc.) adapted to be placed in substantial proximity to a skin surface under treatment. In some embodiments, the contact elements 122 can be a metallic, plastic, or other type of support structure that maintains a desired distance between at least part of the device 100 and the skin surface under treatment to thereby ensure that the desired amount of optical radiation is being applied to the skin surface. The Optical Subsystem 106 may optionally include one or more reflective or absorptive filters 118 to substantially remove or reduce unwanted wavelengths from the emitted optical radiation to the extent that such unwanted wavelengths exceed a desired threshold and are not otherwise eliminated, reduced, or converted by the brightness-enhancers 114, optical waveguides 120, contact elements 122 and/or wavelength converters (not shown).

Exemplary light sources 112 can include one or more flashlamps, lasers, LEDs, or other sources of optical radiation in substantially any suitable quantity, configuration, or combination thereof. For clarity, the bulk of this disclosure will focus on flashlamp embodiments, but this should not be misconstrued to imply that other types of light sources cannot be used. An exemplary light source 112 can be a krypton or xenon flash lamp exhibiting optical radiation emissions that preferably include peaks in the near infrared region of the electromagnetic spectrum, which is preferred for hair growth management/removal dermatologic treatments. In order to maintain a small size and relatively low cost in a handpiece (not shown) of a device 100 designed for home use (the housing of the handpiece preferably contains the light source 112), the Power Subsystem 104 can be configured to overdrive the light source 112, thereby reducing the usable life of the light source 112 in favor of maintaining a small size and desired fluence levels (e.g., 5-10 Joules/centimeter squared for temporary hair growth management), while incurring a relatively low replacement cost for the flashlamp light source 112. The degree to which the flashlamp light source 112 is overdriven can be designed not only to meet the efficacy requirements of a particular dermatologic procedure, but also to effectively support a minimum number of dermatologic treatments before being replaced. Replacement of the relatively inexpensive light source 112 can be facilitated by packaging the flashlamp light source 112 in a replaceable cartridge that can be readily inserted into/out of the housing of the device's handpiece. In this illustrative embodiment, a planned replacement interval (based on, for example, the number of times the light source 112 has been energized, the number of dermatologic treatment sessions performed, etc.) for the flashlamp light source 112 enables the light source 112 to operate at substantially peak efficiency without experiencing an otherwise slow degradation in performance potentially resulting in a reduced efficacy in the dermatologic procedure. Other embodiments may involve operating the light source 112 in accordance with its standard operating parameters that would extend the lifespan of the light source 112 at the expense of a larger size in the light source and a slow degradation in performance.

As described previously, an illustrative brightness-enhancer 114 can be employed to reflect some of the optical radiation emitted by the light source 112 (e.g., unwanted wavelengths) back to the light source 112 so as to increase the brightness of such source 112 (without requiring additional electrical drive energy to the light source 112) and thereby substantially increase the efficiency of the flashlamp light source 112 (with respect to the desired wavelengths of about 600-1100 nanometers) and filter out some of the unwanted wavelengths (e.g., below 600 nm and/or above 1100 nm) at the same time. The brightness-enhancer 114 can include multiple coatings of reflective materials that are preferably optimized to reflect particular unwanted wavelengths and may be arranged in substantially any desired shape using, for example, chemical vapor deposition processes. Illustrative orientations of such brightness-enhancers 114 are further described below in connection with FIGS. 3-6.

Figure 2:
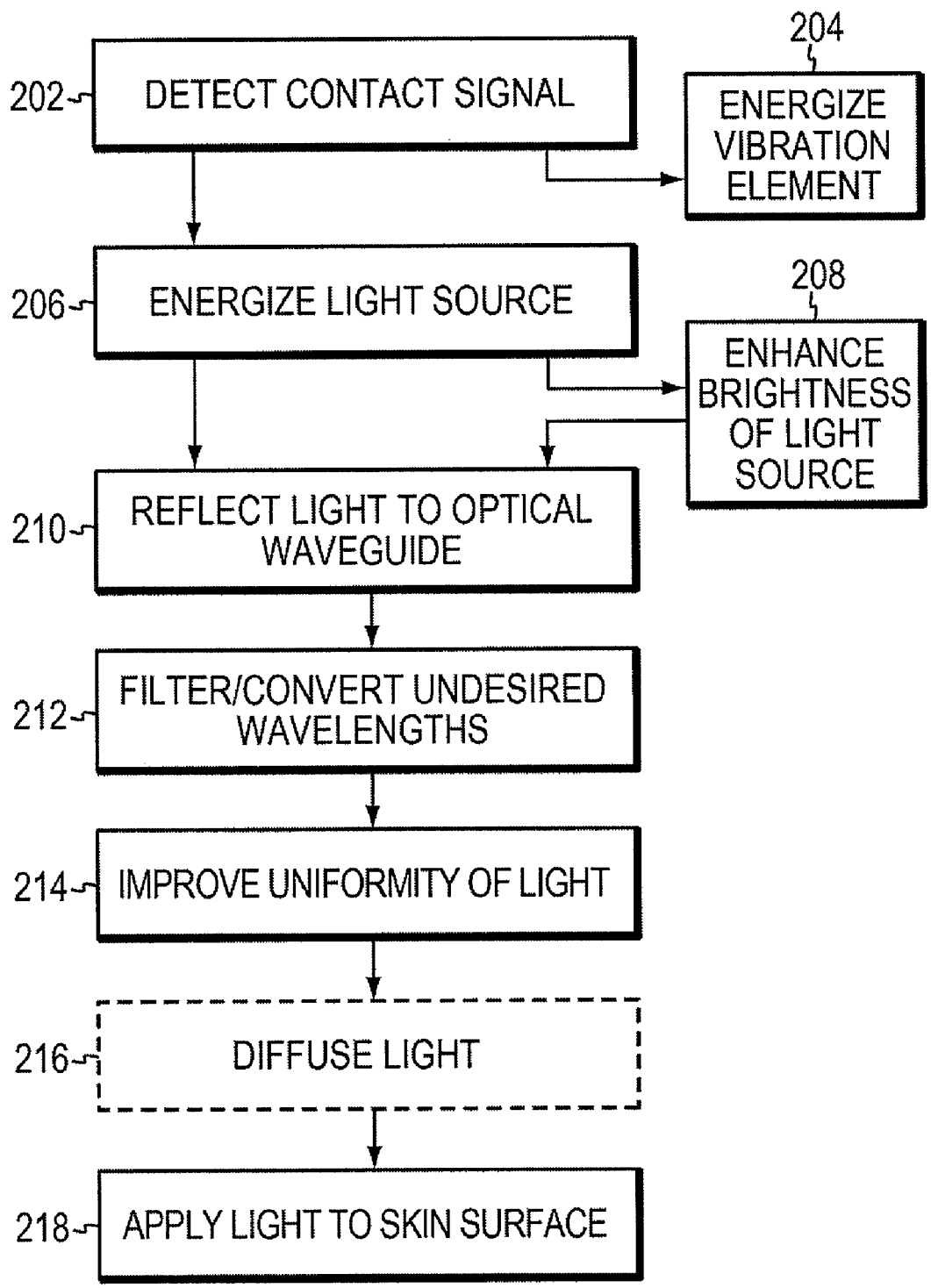
FIG. 2 provides an illustrative methodology for operating the dermatologic treatment device of FIG. 1.

In one illustrative operation and with reference now also to FIG. 2, the Sensor Subsystem 108 detects a contact signal generated when the contact sensors of the device 100 are triggered indicating when the device 100 is in physical contact with the skin surface targeted for dermatologic treatment (202). In response to receiving an indication of the contact signal from the Sensor Subsystem 108, the User Interface and Control Subsystem 102 enables the Power Subsystem 104 to energize the vibration element of the Sensation-Inhibition Subsystem 110 so as to apply sensation-inhibition stimuli to the skin surface to be treated (204). In some embodiments, the vibration element may be energized upon powering up the device 100 and prior to detection of the contact signal. The User Interface and Control Subsystem 102 further enables the Power Subsystem 104 to energize the light source 112 so that it emits a light pulse, or a sequence of continuous light pulses (206). Depending on the particular brightness-enhancer 114 implemented in the device 100, at least some of the emitted optical radiation will be reflected back and superposed onto the directly emitted optical radiation from the light source 112 so as to enhance the brightness of the light source 112 (208). The directly-emitted optical radiation and the brightness-enhanced optical radiation is received and reflected by the reflector 116 towards an input face of the optical waveguide 120 (210). The filter 118 can then filter out at least some of the undesired wavelengths from the optical radiation and/or at least some of the undesired wavelengths can be converted into desirable wavelengths (using, for example, phosphor material, quantum dot material, and/or luminescent dopant material embedded in the optical waveguide 120) (212). The optical waveguide 120 or any other type of optical integrator (e.g., spherical reflector) improves the uniformity of the optical radiation it conveys to avoid optical hot spots (214). The optical radiation transmitted through at least one output face of the optical waveguide 120 can be optionally diffused by, for example, passing the optical radiation through a diffusing portion of the contact element 122 (216). The optical radiation is preferably applied to the skin surface via the contact element 122 which is substantially in contact with the skin surface (218).

Figure 3:
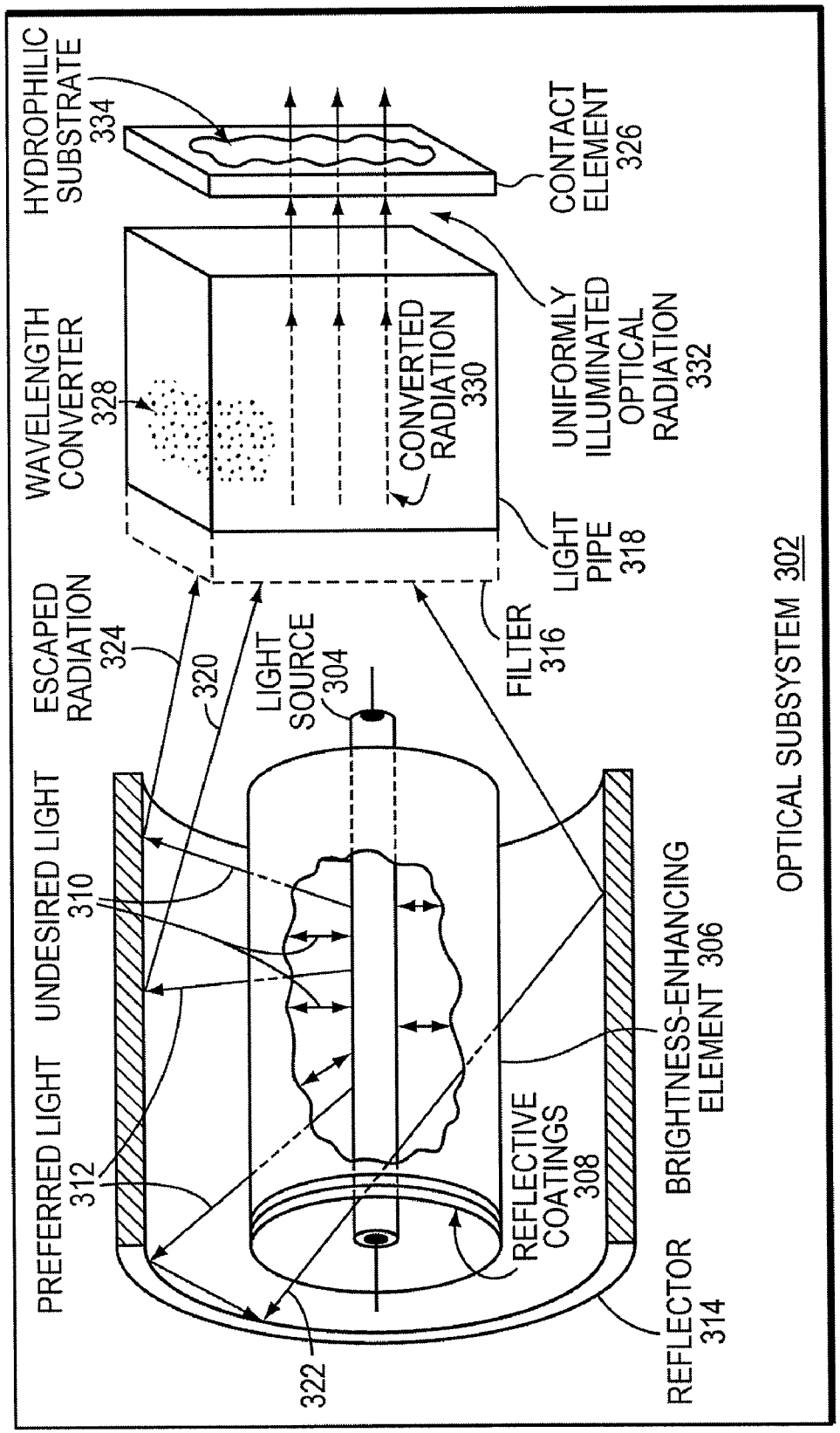
FIG. 3 is a partial, three-dimensional representation of the dermatologic treatment device of FIG. 1 illustrating a preferred orientation and arrangement of its optical elements.

A particularly advantageous embodiment of an Optical Subsystem 302 is illustrated in FIG. 3. The light source 304 is preferably one or more xenon or krypton flashlamps (only one shown for clarity). The light source 304 is substantially surrounded by a tubular brightness-enhancing element 306 exhibiting multiple reflective coatings 308 adapted to substantially reflect undesired wavelengths 310 and pass preferred wavelengths 312. The enhancing element 306 is preferably sized to leave sufficient space between the outer diameter of the light source 304 and the inner diameter of the enhancing element 306 to enable the flow of cooling air to remove excess heat from the light source 304 and enhancing element 306.

The preferred wavelengths 312, which include directly emitted optical radiation and brightness-enhanced optical radiation, successfully pass through the reflective coatings 308 of the enhancing element 306 and are reflected by an ellipsoid reflector 314 (whose reflective surfaces may, for example, include gold, silver, aluminum, etc.) towards an optional filter 316 and then on to a light pipe 318. The preferred wavelengths 312 may pass through the enhancing element 306 once (see light ray 320) or be reflected by the reflector 314 back through the enhancing element 306 one or more times prior to reaching the filter 316 and light pipe 318 (see light ray 322). In some instances, any such preferred wavelengths 312 that are reflected back through the enhancing element 306 may either again pass substantially unimpeded through the enhancing element 306 or be absorbed by the light source 304 and thereby also contribute to the enhanced brightness of subsequently-emitted optical radiation.

Some of the undesired wavelengths 310 may be able to escape the reflective filtering effect of the enhancing element 306 (see light ray 324) and will be substantially and absorptively filtered by the filter 316, light pipe, and/or contact element 326. Alternatively, or in conjunction, any such escaped optical radiation (e.g., light ray 324) can be subjected to one or more fluorophores, such as a phosphor material or other wavelength converter 328 (e.g., quantum dots, luminescent dopant material, etc.) embedded in the light pipe 318 to convert the undesired wavelengths of the escaped optical radiation 324 into preferred wavelengths (see converted-radiation light ray 330).

In an illustrative embodiment, where the wavelengths of the preferred light 312 are in the range of about 600 nm-1100 nm and the light source 304 also emits undesired light 310 on both sides of this range, the disclosed technology can be used to reflect that portion of the undesired light 310 exhibiting wavelengths longer than 1100 nm back to the light source 304 to increase overall brightness and the portion of the undesired light 310 exhibiting wavelengths shorter than 600 nm can be converted into longer wavelengths within the range of the preferred light 312 by the wavelength converter 328. For example, the undesired light 310 exhibiting wavelengths shorter than 600 nm can be converted to longer wavelengths in the near infrared part of the electromagnetic spectrum (NIR wavelengths are preferred for hair growth management/removal) by passing such shorter wavelengths through quantum dot compositions that are tuned (with respect to composition, size, and/or shape) to emit desired wavelengths. Exemplary quantum dot compositions that may be used to emit near infrared optical radiation can include a core comprised of CdTe, InAs, InP, InSb, PbS, and/or PbSe and are preferably encapsulated in an overcoating layer (e.g., ZnS, ZnSe, GaN, MgS, MgSe, MgTe, CdS, or CdSe), which preferably enhances efficiency, quantum yield, and photostability without substantially modifying the wavelength emissions of the core. Quantum dot compositions may be substantially homogeneous in size, shape, or core/overcoat elements in embodiments in which a relatively narrow set of emission wavelengths are desired or can be heterogeneous in embodiments requiring a somewhat broader set of emission wavelengths. In an illustrative heterogeneous implementation, it may be preferable to have incident light impinge first on quantum dots that emit the longest wavelengths desired and subsequently impinge on other quantum dots whose desired emissions are successively shorter in wavelength. In this manner, the relatively longer wavelength emissions of a first layer of quantum dot material will not be adversely affected by subsequent layers that could otherwise reabsorb such wavelengths and emit other wavelengths. In some embodiments, heterogeneous implementations can reverse the order of such layers or intermix various combinations of quantum dots. In some embodiments, a wavelength selection element (e.g., one or more prisms, diffraction gratings, interference filters, etc.) (not shown) may be used to separate at least some of the undesired light (e.g., wavelengths shorter than 600 nm) from the other optical radiation emissions of the light source 304 and then subject such separated, undesired light to appropriate quantum dot compositions to provide a wavelength conversion effect without substantially converting any of the other wavelengths.

The optical radiation 332 exiting the output face of the light pipe 318 preferably exhibits a uniform illumination to avoid any undesired radiation hot spots. This uniformly illuminated radiation 332 is passed through the contact element 326, which may include a hydrophilic substrate coating 334 at the skin-device interface to facilitate movement of the dermatologic treatment device over or to the skin surface/region targeted for treatment. The hydrophilic substrate 334 can be formulated, in some embodiments, to filter out ultraviolet or other undesired wavelengths 324 that escaped filtration/conversion by other elements of the Optical Subsystem 302.

Figure 4:
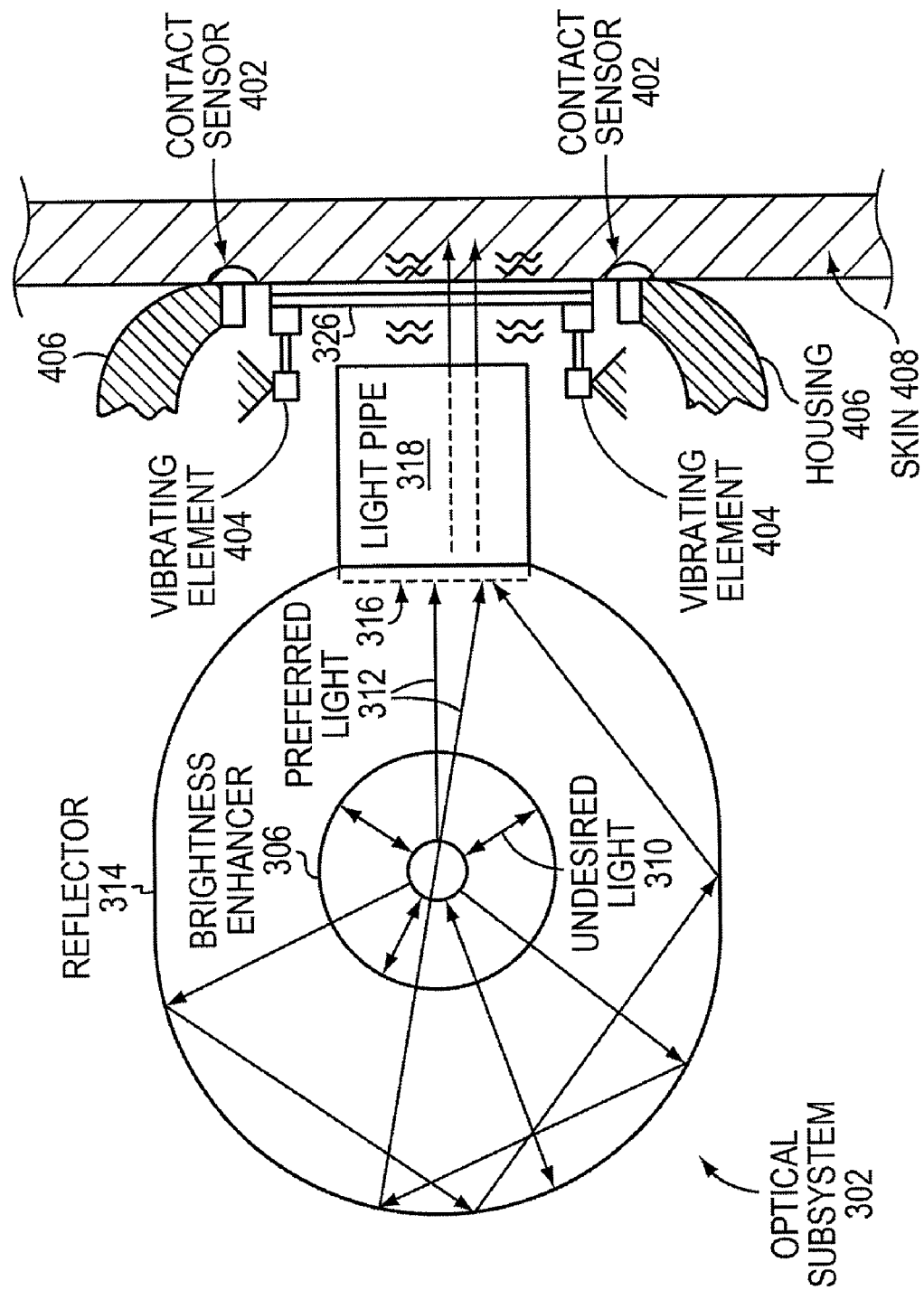
FIG. 4 provides a cross-sectional representation of the optical elements of the dermatologic treatment device of FIG. 1 illustrating an exemplary conveyance of optical radiation using a brightness enhancer in conjunction with a vibrating contact element.

A cross-sectional view of the Optical Subsystem 302 of FIG. 3 is depicted in FIG. 4 to more particularly illustrate exemplary locations of contact sensors 402 and vibrating elements 404. The contact sensors 402 can be mounted in a housing 406 forming a handpiece of the dermatologic treatment device and such sensors 402 can be positioned to contact the skin 408 at a location that is substantially proximal to the contact element 326 to thereby ensure that optical radiation emitted through the contact element 326 is substantially proximal to the skin surface to be treated at the time of treatment. Alternatively, the contact sensors 402 can be incorporated into or otherwise be physically coupled to the contact element 326. The exemplary vibrating elements 404 are shown mounted between the housing 406 and the contact element 326, which contact element 326 may be mounted on a spring mechanism (not shown) to vibrationally separate the contact element 326 from the housing 406, thereby causing the contact element 326 to provide the bulk of the sensation-inhibition stimuli to the skin rather than the housing 406. Alternatively, the vibrating elements 404 can be configured to substantially vibrate that portion of the housing 406 that is in contact with the skin 408 (which may or may not also cause the contact element 326 to vibrate depending on the desired implementation) or may vibrate the entirety of the housing including portions that are and are not in contact with the skin 408.

With reference now to FIGS. 5A-D, several additional illustrative embodiments are depicted for arc-shaped, brightness enhancers that may be used to achieve the brightness-enhancement benefit described in this disclosure. These brightness enhancers can, in some cases, be adapted to reflect back all of the wavelengths in the impinging optical radiation or just subsets of wavelengths that are not desired for a particular dermatologic treatment, as previously described. Although the cross-sectional representations of the reflector 502, light source 504, and optical waveguide 506 depicted in each of FIGS. 5A-D are identical, those skilled in the art will recognize that a large variation in such elements 502-506 can be implemented in different embodiments of a dermatologic treatment device and that the sole purpose of showing these elements 502-506 as being identical is to facilitate illustration of different orientations, configurations, and relative locations of the arc-shaped, brightness enhancers 508-514.

Figure 5A:
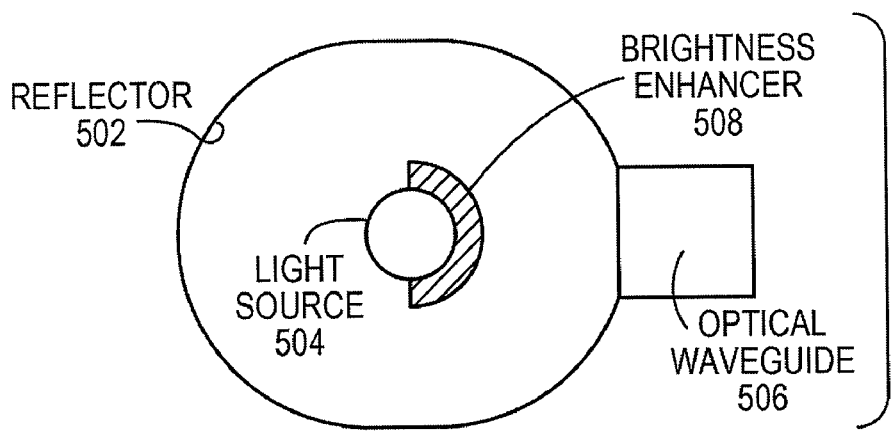
FIGS. 5A-D provide cross-sectional representations of several illustrative arc-shaped, brightness enhancers that represent certain aspects of the disclosed technology.

FIG. 5A depicts an arc-shaped brightness enhancer 508 that is configured in a substantially hemispherical shape to cover that half of the light source 504 that faces the optical waveguide 506. In this embodiment, the brightness enhancer can be formed as reflective coatings/film directly in contact with an outer or inner surface of the quartz enclosure of the flashlamp light source 504 or can be formed on another material (e.g., polished surface of a metallic hemispherical reflector, quartz support member with hemispherical shape, etc.) that is placed substantially in contact with the light source 504. This embodiment is also beneficial in situations where it is desired to periodically replace both the light source 504 and the enhancer 508 as a single unit to ensure peak performance of the system during dermatologic treatments as previously described.

Figure 5B:
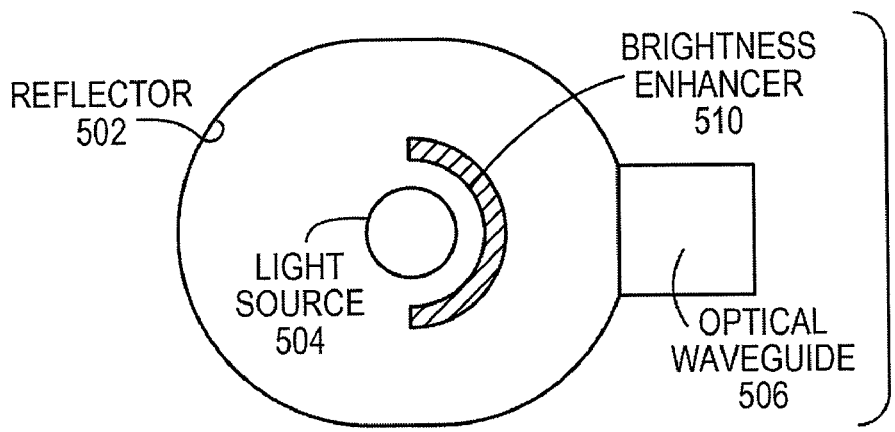

FIG. 5B depicts an arc-shaped brightness enhancer 510 that is substantially similar to the hemispherical shape of the enhancer 508 shown in FIG. 5A, except that it is located some distance away from the flashlamp light source 504 (e.g., far enough away so that any impinging optical radiation will be substantially perpendicular at its point of contact and thus be optimally reflected back into the plasma of the flashlamp light source 504. The separation distance, whether optimal or not, may also improve the cooling of the flashlamp 504 and/or enhancer 510, and thereby extend the life of the flashlamp 504 and prevent undesirable damage to the coatings of the enhancer 510. As with FIG. 5A, this FIG. 5B embodiment facilitates periodic replacement of the light source 504 and enhancer 510, except that it also provides the additional benefit of selectively being able to replace the light source 504 or the enhancer 510 separately or as a single light source-enhancer unit.

Figure 5C:
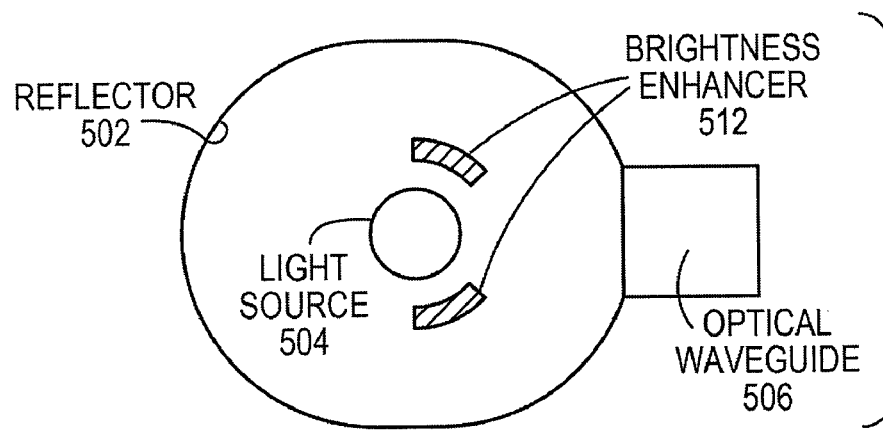

FIG. 5C depicts a variation of the arc-shaped brightness enhancer 510 of FIG. 5B in that multiple enhancer elements 512 can be used in reflecting back some of the optical radiation emitted by the flash lamp 504 that may otherwise result in too many reflections by the reflector 502 prior to entering the optical waveguide 506. The particular design details for such enhancers 512 can be based on, for example, a threshold of how much anticipated absorption is to be tolerated by the reflector 502 prior to transmitting the optical radiation to the optical waveguide 506.

Figure 5D:
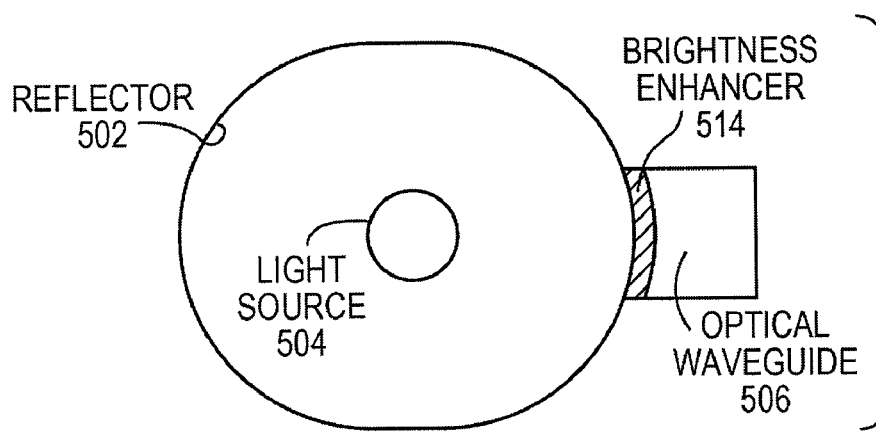

FIG. 5D depicts an arc-shaped brightness enhancer 514 that is formed on an input face of the optical waveguide 506. Unlike the embodiments of FIGS. 5A-C in which those enhancers 508-512 could be designed to either reflect back all impinging wavelengths or just wavelengths that are not desired for a particular dermatologic treatment, the enhancer 514 of this embodiment must be designed to reflect back only some, but not all wavelengths, otherwise the emitted radiation would not be transmitted forward to the optical waveguide 506. Benefits of this embodiment, include maximizing cooling airflow between the light source 504 and enhancer 514 and/or reduced mounting support structures for the enhancer 514.

Figure 6A:
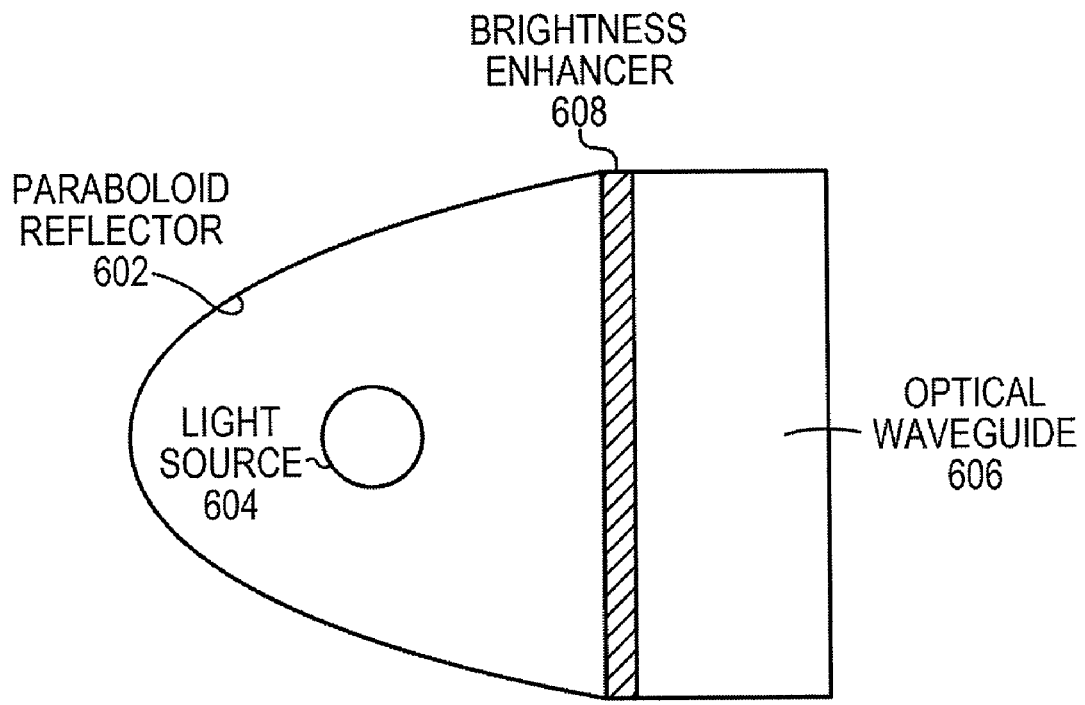
FIGS. 6A-B provide cross-sectional representations of several illustrative planar-shaped, brightness enhancers that represent certain aspects of the disclosed technology.
Figure 6B:
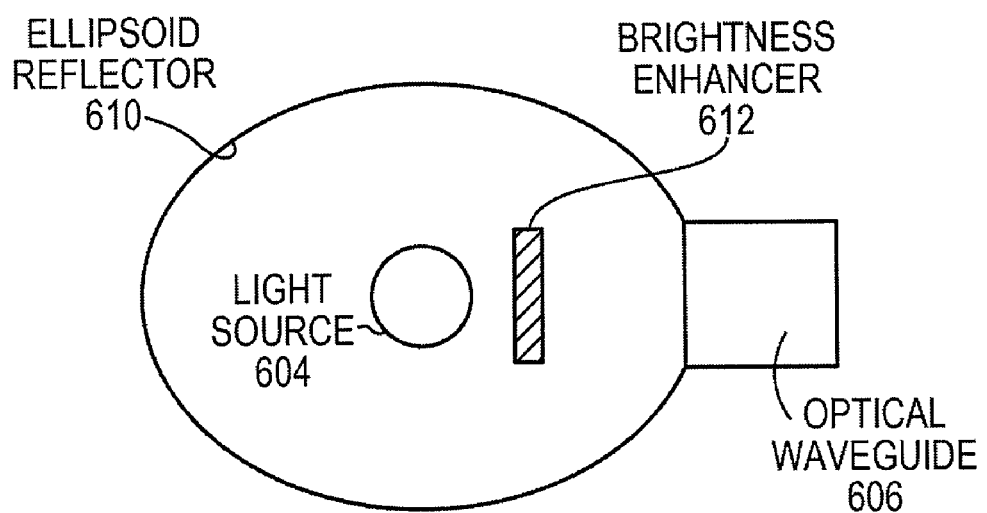

With reference now to FIGS. 6A-B, several additional illustrative embodiments are depicted for planar-shaped, brightness enhancers that may be used to achieve the brightness-enhancement benefit described in this disclosure. As described above in connection with arc-shaped enhancers, these brightness enhancers can also be adapted to, in some cases, reflect back all of the wavelengths in the impinging optical radiation or just reflect subsets of wavelengths that are not desired for a particular dermatologic treatment. Although the cross-sectional representations of the light source 604, and optical waveguide 606 depicted in each of FIGS. 6A-B are identical, those skilled in the art will recognize that a large variation in such elements 602-606 can be implemented in different embodiments of a dermatologic treatment device and that the sole purpose of showing these elements 604-606 as being identical is to facilitate illustration of different orientations, configurations, and relative locations of the planar-shaped, brightness enhancers 608-610.

FIG. 6A depicts a planar-shaped brightness enhancer 608 that is formed on an input face of the optical waveguide 606. Although the reflection attributes of this enhancer 608 require that only some of the wavelengths be reflected back to the light source 604, this embodiment can result in significant cost savings and reduce complexity in the manufacturing process for the enhancer 608 and will further maximize the volume available for cooling airflow between the light source 604 and the enhancer 606, as well as reducing the mounting support structures for the enhancer 608 and associated costs.

FIG. 6B depicts a planar-shaped brightness enhancer 612 that is substantially similar to the planar shape of the enhancer 608 shown in FIG. 6A, except that it is spaced apart from both the flashlamp light source 604 and the optical waveguide 606 (the distances between such enhancer 612 and elements 604, 606 may, but need not be equidistant). As with FIG. 5B, this FIG. 6B embodiment facilitates periodic replacement of the light source 604 and enhancer 612, separately or as a single light source-enhancer unit.

Figure 7:
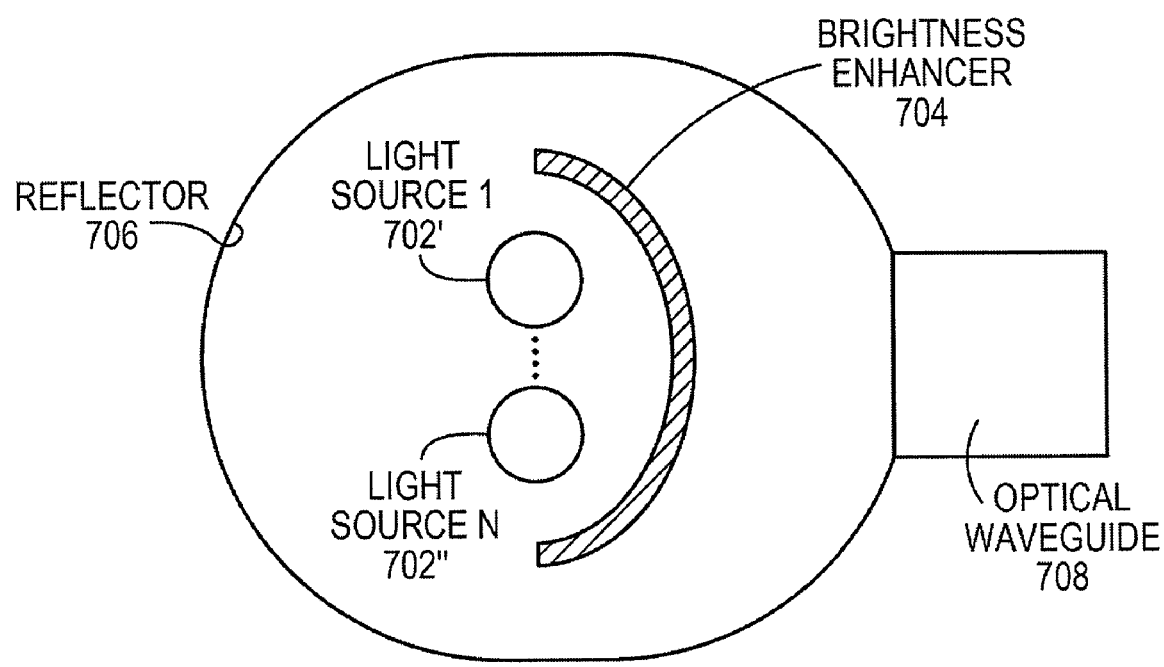
FIG. 7 provides a cross-sectional representation of an exemplary optical subsystem configuration in which multiple light sources are used in conjunction with a brightness enhancer.

FIG. 7 depicts an illustrative embodiment in which multiple light sources 702 (such as two or more flashlamps) are positioned substantially adjacent to each other and energized substantially at the same time or during overlapping time intervals so that, for example, at least some light emitted from light source 1 702' impinges upon and thereby enhances the brightness of light source N 702" and vice verse. Energizing flashlamp light sources 702' and 702" sequentially (e.g., with substantially no inter-pulse delay or with an inter-pulse delay interval that is less than the thermal relaxation time of a skin surface under treatment) or with some overlap enables a particular skin surface to be treated for a relatively long duration of time without unduly overdriving the light sources 702' and 702". A brightness enhancer 704 can be positioned around at least part of the light sources 702 so as to further enhance the brightness of both light sources. The light sources 702' and 702" may be adapted to emit optical radiation with substantially the same spectral characteristics, different spectral characteristics, or overlapping spectral characteristics. The light sources 702' and 702" may further be of the same type (e.g., flashlamps) or of different types (e.g., combinations of flashlamps, lasers, and/or LEDs). The brightness enhancer 704 can be implemented in a variety of shapes, sizes, orientations, and may further include more than one brightness-enhancing element. In embodiments, where multiple brightness enhancers are used, such brightness enhancers can have substantially the same light reflecting effect on the light sources 702' and 702" or may be designed to have different light reflecting effects on such light sources 702'-702". In some embodiments one or more brightness enhancers may have an effect on light source 1 702' but have substantially no effect or a lessened effect on light source N 702".

Figure 8A:
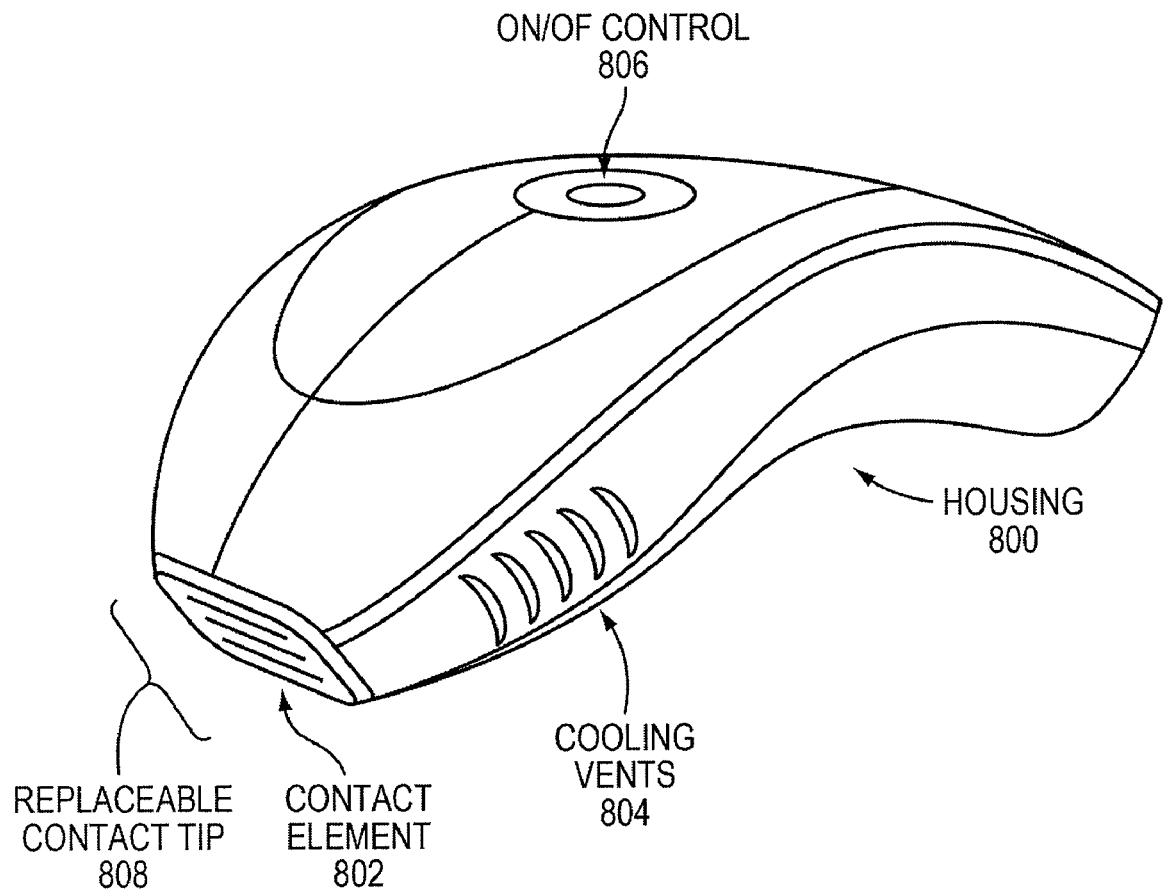
FIGS. 8A-B are perspective drawings of an exterior of an illustrative housing suitable for supporting the optical components of a dermatologic treatment device in accordance with certain aspects of the disclosed technology.
Figure 8B:
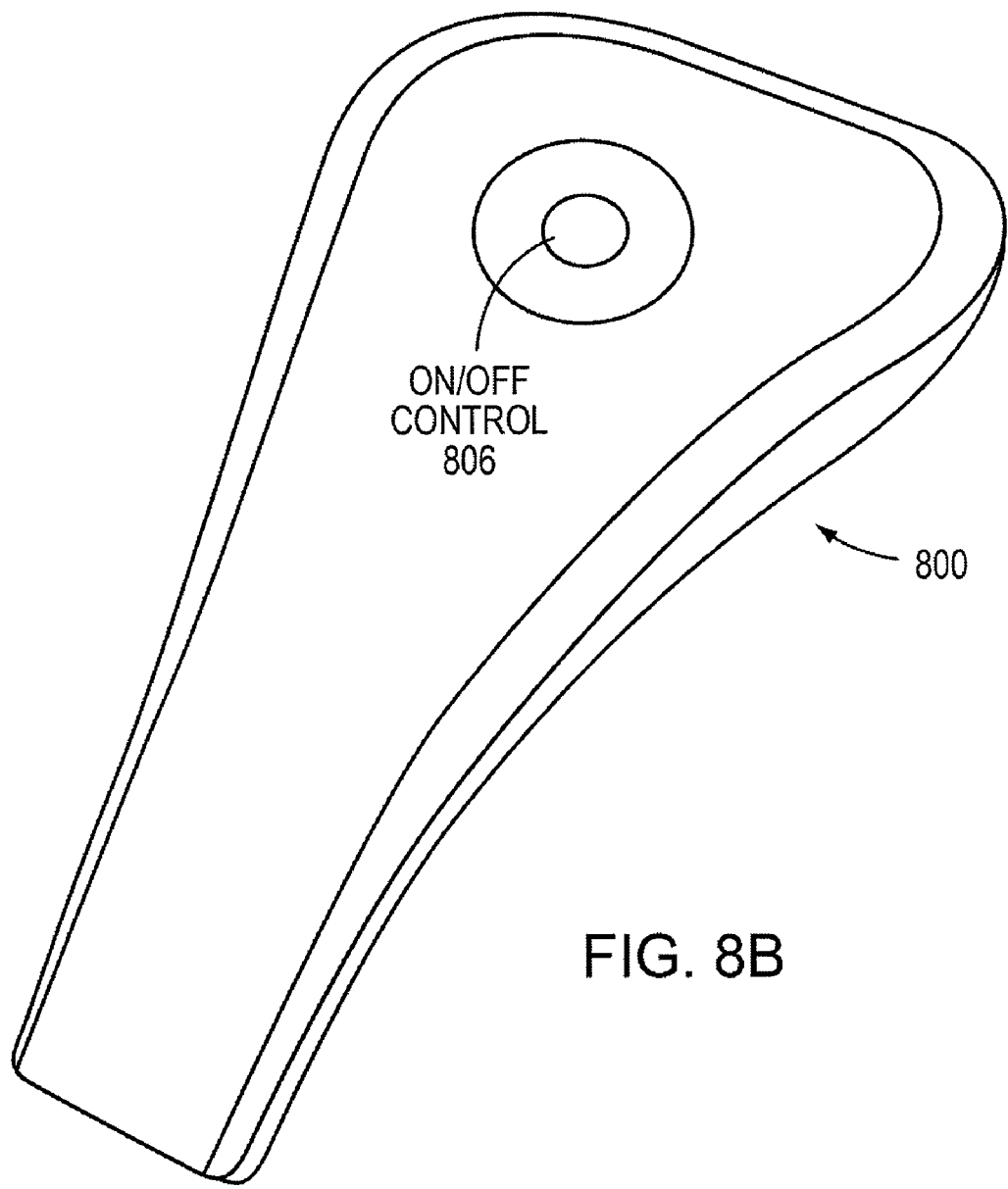

With reference to FIGS. 8A-B, at least some aspects of the disclosed technology can be incorporated within a handheld housing 800 of a dermatologic treatment device. For example, the housing 800 preferably encloses optical subsystem components with a surface of a contact element 802 being exposed for placement against a skin surface to be treated. The housing includes cooling vents 804 that are used to draw in and/or exhaust cooling air applied to one or more of the components of the optical subsystem. User interface and control elements, such as an on/off switch 506 are provided in a location that is readily accessible to a user during operation of the dermatologic treatment device. The housing 800 further contains contact sensors and sensation-inhibition elements (not shown). In one illustrative embodiment, the housing 800 includes a replaceable contact tip 808 that includes the contact element 802. This replaceable contact tip 808 improves upon the sanitary use of the device by enabling a user to replace skin contact surfaces of the device between dermatologic treatments of the same/different individual(s) or during a single dermatologic treatment applied to different skin surfaces.

Figure 9:
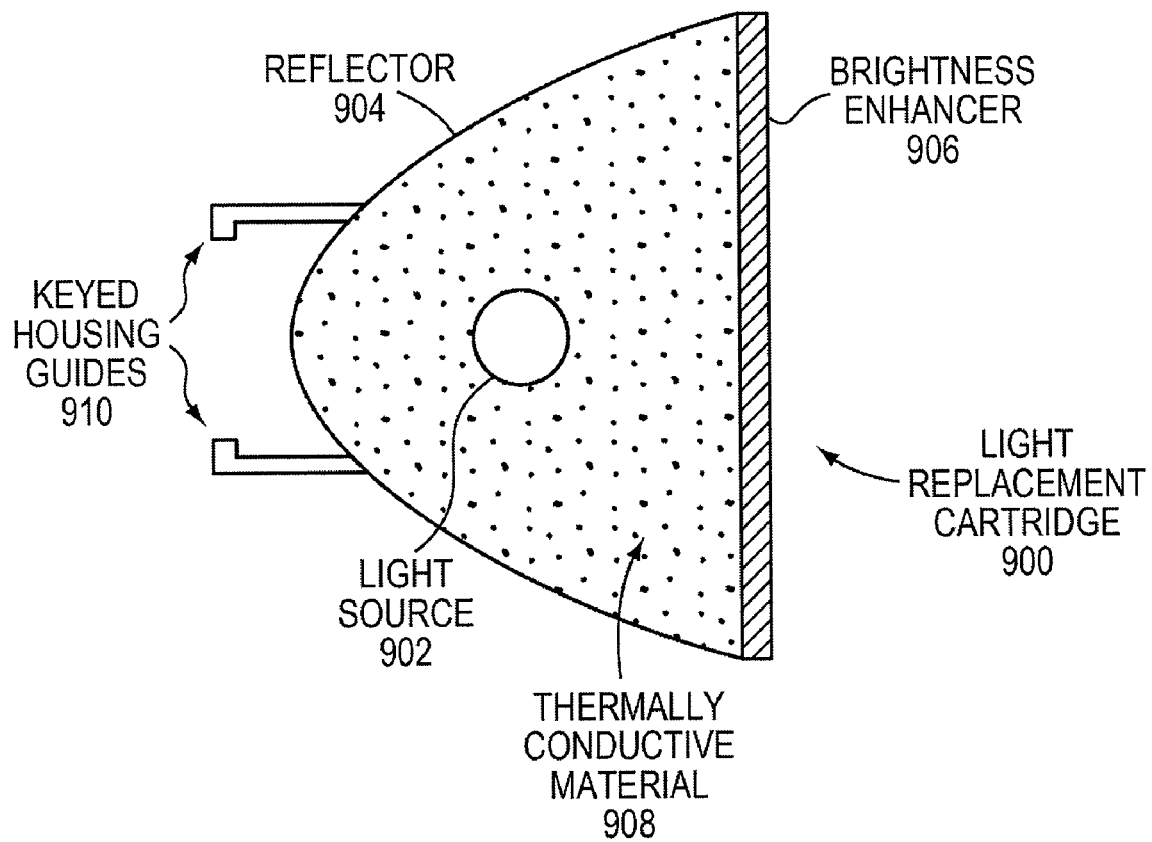
FIG. 9 provides a cross-sectional representation of an exemplary light replacement cartridge that may be removable from/insertable into the housing of FIG. 8 by a user of the dermatologic device in accordance with certain aspects of the disclosed technology.

With reference now also to FIG. 9, the housing 800 of FIGS. 8A-B preferably includes a light-replacement cartridge 900 that is removable from/insertable into the housing 800 by a user of the dermatologic device in accordance with certain aspects of the disclosed technology. The light replacement cartridge 900 preferably includes one or more light sources 902, a reflector 904, one or more brightness enhancers 906, thermally conductive material 908 disposed at least between the light sources 902 and the reflectors 904, and keyed housing guides 910 adapted to ensure that the light replacement cartridge is of an approved type and is properly inserted into the housing 800 (FIG. 8) during a replacement procedure. The thermally conductive material 908 can be a liquid (such as water, a solution, suspension, etc.), a solid, and/or a gas that is adapted to efficiently conduct heat from the light source 902 to the reflector 904 (which subsequently transfers the heat to a heat sink and/or is air cooled), while concurrently conveying optical radiation in a desired manner. The thermally conductive material 908 may further be homogeneous or heterogeneous in its composition. The thermally conductive material 908 may also include wavelength conversion material (such as quantum dots) to convert undesired wavelengths emitted by the light source 902 into preferred wavelengths while concurrently using at least some of any optical radiation backscattered from such wavelength conversion material to further enhance the brightness of the light source 902. The replacement procedure may be initiated, for example, in the event that different skin types are to be treated (in which it may be desirable to insert optical components that are optimized for such skin type), upon failure of the light source 902 or other system component, upon indication by a user interface and control subsystem, and/or upon release of improvements/corrections in the light cartridge components made by a manufacturer thereof. Although the cartridge 900 may contain each of these components, those skilled in the art will recognize that the cartridge 900 may contain fewer components (such as, for example, only the light source 902, reflector 904, and thermally conductive material 908, or substantially any other combination of components).

While a number of embodiments and variations thereon have been described above, it is intended that these embodiments are for purposes of illustration only and that numerous other variations are possible while practicing the teachings of the disclosed technology. For example, the disclosed technology has been largely described in connection with hair growth management/removal applications, but can be applied to a wide variety of medical or cosmetic dermatologic treatments. The particular type, quantity, and orientation of optical radiation sources, brightness-enhancing elements, and other optical, mechanical, chemical, electrical, and/or physical aspects of the disclosed technology are also illustrative and can be readily modified without materially departing from the teachings of this disclosure. Thus, while the invention has been particularly shown and described above with reference to preferred embodiments, the foregoing and other changes in form and detail may be made therein by one skilled in the art without departing from the spirit and scope of the invention which is to be defined only by the appended claims.

What is claimed is:

1. A dermatologic treatment device, the device comprising:
    a light source emitting at least some optical radiation beneficial to at least one dermatologic treatment;
    a reflector optically coupled to and at least partially surrounding the light source, the reflector reflecting the emitted optical radiation in a predetermined manner,
    a thermally conductive material disposed at least between and in thermal communication with the light source and reflector, the thermally conductive material facilitating a transfer of heat from the light source to the reflector;

a handheld housing enclosing a removable replacement cartridge, the replacement cartridge containing the light source, reflector, and thermally conductive material, the replacement cartridge further comprising housing guides extending from an exterior surface of the replacement cartridge for guiding insertion of the replacement cartridge within the housing, the replacement cartridge facilitating replacement of the light source, reflector, and thermally conductive material by a user of the device between dermatologic treatments.

2. The device of claim 1, wherein optical radiation emitted by the light source includes a first set of wavelengths and a second set of wavelengths, wherein the first set of wavelengths is preferred for the dermatologic treatment.

3. The device of claim 2, wherein the thermally conductive material includes a composition of quantum dots adapted to convert at least some of the second set of wavelengths into first set of wavelengths.

4. The device of claim 1, wherein the replacement cartridge is designed for a particular skin type.

5. The device of claim 1, wherein the replacement cartridge further comprises keyed housing guides extending from an exterior surface of the reflector.

* * * * *